United States Patent [19]

Mendiratta

[11] 4,400,555
[45] Aug. 23, 1983

[54] ION EXCHANGE CATALYZED BISPHENOL SYNETHESIS

[75] Inventor: Ashok K. Mendiratta, Schenectady, N.Y.

[73] Assignee: General Electric Company, Schenectady, N.Y.

[21] Appl. No.: 309,144

[22] Filed: Oct. 6, 1981

[51] Int. Cl.³ .............................................. C07C 39/16
[52] U.S. Cl. .................................. 568/728; 568/722; 568/723; 568/727
[58] Field of Search ............... 568/727, 728, 722, 723, 568/726

[56] References Cited

U.S. PATENT DOCUMENTS

| | | | |
|---|---|---|---|
| 2,775,620 | 12/1956 | Williamson | 568/728 |
| 3,049,568 | 8/1962 | Apel et al. | 568/728 |
| 3,049,569 | 8/1962 | Apel et al. | 568/728 |
| 3,153,001 | 10/1964 | Apel et al. | 568/722 |
| 3,172,916 | 3/1965 | Wagner | 568/728 |
| 3,394,089 | 7/1968 | McNutt et al. | 568/728 |
| 4,191,843 | 3/1980 | Kwantes et al. | 568/728 |
| 4,294,995 | 10/1981 | Faler et al. | 568/728 |
| 4,308,404 | 12/1981 | Kwantes et al. | 568/728 |

Primary Examiner—Werren B. Lone
Attorney, Agent, or Firm—William A. Teoli; James C. Davis, Jr.; James Magee, Jr.

[57] ABSTRACT

An improved bis-phenol synthesis reactor system is provided using multiple acetone injection in an ion exchange catalyzed BPA synthesis process. This process results in an improved reactant effluent product distribution and color.

7 Claims, 1 Drawing Figure

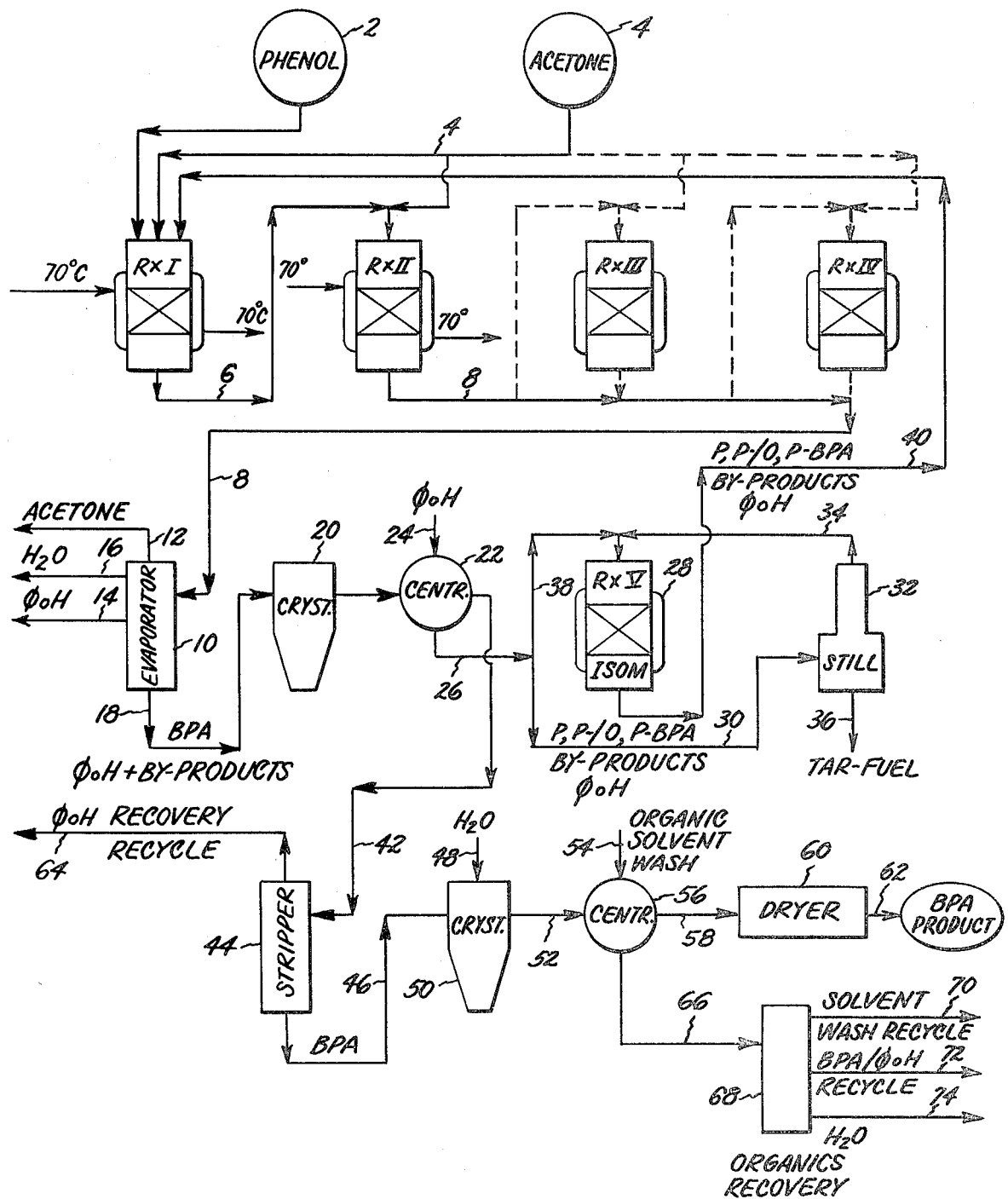

ION EXCHANGE CATALYZED BISPHENOL SYNETHESIS

Prior to the present invention various methods were employed to synthesize bisphenols, such as bisphenol-A, by effecting reaction between a ketone and phenol. One procedure, for example, involved the use of large amounts of inorganic acid catalysts, such as sulfuric acid or hydrochloric acid. Experience has shown, however, that the use of inorganic acids requires a means to neutralize such acids at the end of the reaction due to the corrosive action of the strong acids. In addition, distillation of the resulting bisphenol is often required because of the many by-products formed during the reaction under high acid conditions.

An improved procedure was developed byusing a solid resin cation-exchange catalyst to effect the condensation between the phenol and the ketone. However, the disadvantage of the ion-exchange catalyst is the low acid concentration it provides, resulting in the need for a rate accelerator such as a mercaptan. One procedure is shown by Apel et al. U.S. Pat. No. 3,153,001, which incorporates the mercaptan by partial esterification of the ion-exchange catalyst in the form of a sulfonated insoluble polystyrene resin. Another procedure involves the partial neutralization of such sulfonic acid moity with an alkyl mercapto amine, as shown by McNutt et al. U.S. Pat. No. 3,394,089. A further procedure is shown by Wagner et al. U.S. Pat. No. 3,172,916, based on the partial reduction of the sulfonic acid to afford thiophenol functional groups.

Williamson, U.S. Pat. No. 2,775,620, reported that in a mineral acid catalyzed BPA manufacturing process, higher purity BPA products can be recovered by injecting between 50–75% of the acetone to the first reactor and the balance to the second reactor, all the phenol being injected to the first reactor, in a two-reactor (in series) system. Williamson, describes a multiple acetone injection concept which is applicable to mineral acid catalyzed systems (with bulk mercaptan addition) for BPA synthesis. High residence time is given in the reactor (batch or continuous) and acetone conversion of about 100% is obtained. In the Williamson process the acetone conversion is complete within about 50% of the residence time. At this time the condensation products contain about 70% p,p-BPA, 30% o-p-BPA and by-products. Much of the reaction time in this process is used for equilibration of the products so as to obtain the equilibrium concentration of p,p-BPA which is at about 90% depending on temperature. A substantial amount of isomerization/rearrangement of the BPA synthesis reaction product occurs in the reactor, even in the presence of water which is a reaction product. The reactor effluent is essentially an equilibrium mixture with p,p-BPA: 85–90% and other reaction products: 10–15%.

The present invention relates to a multiple acetone injection, mercaptoamine neutralized cation exchange catalyzed, fixed bed reactor system. Substantially different chemistry and kinetics are involved in the present process. Short residence time is given in the reactor and an acetone conversion of 60–70% is obtained. The present process, unlike the acid catalyzed system, results in condensation products containing about 95% p,p-BPA which is well above the 90% p,p-BPA concentration at equilibrium. Because of this, equilibration is not desirable. Negligible equilibration/isomerization/rearrangement of BPA synthesis reaction products occurs in the reactor due to the presence of water which inhibits such reactions in the cation-exchange catalyzed systems. The reactor effluent has 95–96% p,p-BPA and 4–5% other reaction products.

The phenol to acetone ratio in the feed to the reactor system in an ion-exchange catalyzed BPA manufacturing process has a prominent effect upon by-product formation and reactor effluent color. This in turn effects the material usage and BPA product color quality. A high ratio of phenol to acetone is favored as it results in the reduction of by-products formation and lower reactor effluent color. Any excess phenol, however, must be recovered from the reactor effluent and recycled to the reactor. This necessitates higher capital expenditures and operating expenses. The recommended phenol to acetone ratio has been found to be between five and ten molar even though the stiochrometric ratio of phenol to acetone is 2:1.

The present invention describes a process for the preparation of bisphenol-A comprising reacting phenol and acetone in the presence of a cation-exchange resin catalyst in a reactor or alternatively in a series of reactors, wherein all of said phenol and a portion of said acetone necessary for the reaction is charged at the beginning of the reactor or alternatively in the first reactor and the remainder of said acetone is injected along the reactor length or alternatively in subsequent reactors. This procedure allows a high relative phenol concentration to be maintained during most of the process. High purity bisphenol-A is prepared in the substantial absence of undesirable by-products, color bodies, tars and other reaction product impurities.

The process of this invention, because of a reduction in amount of by-product impurities and color formed in the reactor, (1) reduces the amount of by-product impurities which—after separation from the crude bis-phenol-A—are recycled for isomerization in the presence of excess phenol and returned to the reaction zones as a portion of the feed stock as well as (2) reduces the amount of by-product impurities necessarily cracked in a phenol recovery waste process stream carried out in accordance with the teachings of Carnahan in U.S. Pat. No. 4,277,628 and hence reduces the material losses in the system.

The process of the present invention can therefore, result in the following benefits:

(1) For same overall phenol to acetone ratio charged to the reactor system, multiple acetone injection will result in improved reactor effluent product distribution and color, thus yielding high material usage and improved BPA product color; or (2) For same reactor effluent product distribution and color, overall phenol to acetone ratio charged to the reactor system can be reduced by multiple acetone injection, thus reducing the capital/operating costs involved with recovery and recycling excess phenol.

The process of this invention is carried out in a continuous reactor or a series of reactors under kinetic reaction conditions wherein p,p-bisphenol-A is prepared on mole ratio basis in amounts of at least 92% and often amounts as great as 97% relative to the o,p-bisphenol-A formed in conjunction with the well known color bodies, tars and other reaction by-product impurities associated with bis-phenol-A condensation reactions conditions.

Advantageously, the process of this invention describes operating parameters which can be widely varied and which permit the steady state conversion of phenol and acetone to bis-phenol-A under highly desirable reaction conditions which minimize capital and operating costs commonly associated with many of the processes described in the prior art.

More particularly, there is provided by the present invention a process for the production of bis-phenol-A comprising reacting phenol and acetone in the presence of a cation-exchange resin catalyst wherein all of the phenol required for reaction is charged at the beginning of the reactor and the acetone is injected along the reactor length resulting in a mixture of bis-phenol-A, phenol, acetone, water and phenol-acetone condensation by-products. The reactor effluent may then be treated by any conventional means to separate the bis-phenol-A from the by-products and also from the reactants so that they may be recycled, for example, separating a mixture of bisphenol-A and by-products from the phenol, acetone and water by evaporation/distillation; separating the water from the phenol and acetone by distillation/evaporation; returning substantially anhydrous phenol and acetone to the bisphenol-A reactor system; crystallizing the bisphenol-A in the presence of phenol to produce solid bisphenol-A: phenol adduct and a mother liquor containing phenol, bis-phenol-A, and condensation by-products; cracking a minor portion of the mother liquor to form phenol and cracking products; isomerizing a major portion of the mother liquor in the presence of an ion-exchange resin; recycling the isomerization products as well as the phenol from the cracking operation to the first bisphenol-A reactor to provide at least a portion of the feedstock; removing phenol from the solid BPA:phenol adduct by evaporation; crystallizing the crude BPA in the presence of water to yield BPA crystals; washing the BPA crystals with a suitable organic solvent to yield pure BPA product free of any impurities and color bodies.

The present process for conducting the condensation of phenol and acetone to form bisphenol-A can be carried out in accordance with those well established in the art. Mole ratios of phenol and acetone can be from about 2:1 to about 10:1 and as high as about 30:1. Substantially anhydrous reaction conditions can be used whereby the by-product condensation reaction water content of the process is less than 2% and preferably less than 1.5%. Substantially anhydrous feedstock can be utilized, e.g. anhydrous phenol, anhydrous acetone or anhydrous recycle isomerization or cracked condensation products.

Conventional ion-exchange resin catalysts can be used, e.g. strong-acid ion exchange resins, including resins or polymers having a plurality of appended sulfonic acid groups. Examples include sulfonated polystyrene or poly(styrene-divinyl-benzene) copolymers and sulfonated phenol-formaldehyde resins. Specific examples of commercially available resins are; Amberlite ® or Amberlyst ® manufactured by Rohm and Haas, Dowex ® manufactured by Dow Chemical Company, Permutit QH ® manufactured by Permutit Company, Chempro C-20 ® manufactured by Chemical Process Company. As stated before, the acid ion exchange resins can be partially modified by reacting the acidic groups with mercapto alkyl amines, by partially esterifying the acid resins with a mercapto alcohol, or with an alkyl amine precursor such as thiazolidines. The unmodified ion-exchange resins generally have an ion-exchange capacity preferably of at least about 2.0 milliequivalents H+, with exchange capacities in the range of from about 3 to about 5 milliequivalents of H+ per gram of dry resin. About 5% to about 35% or more, preferably from about 15% to about 25% of acid sites are modified by reacting the acid sites with a mercapto group.

The reaction time in the individual reaction zones under steady state reaction conditions can vary widely and will vary with temperature. The reaction can be carried out at between about 50° C. and about 120° C. preferably between about 60° C. and 80° C. The weight hourly space velocity (WHSV) of the reactor feed to the first reactor and the effluent streams subsequently passed to the down stream reactors may vary within the limits of from about 0.05 to about 15 parts by weight of feed stream per part by weight of catalyst per hour. Based on the weight hourly space velocity of the feedstock under steady state reaction conditions, the conversion of acetone can vary widely from as little as about 20% to about 82%

The term bisphenol-A or BPA refers to the commercially important 2,2'-bis(4-hydroxyphenyl)propane. As will be apparent to those of ordinary skill in the art, the process of the invention described herein is applicable to the preparation of bis(hydroxyphenyl)compounds and such compounds are derived by substituting or including, in addition to the reactant phenol (i.e. also known as monohydroxybenzene), other phenolic type reactants including ortho- and meta-cresol; 2,6-dimethyl phenol; ortho-secondary butylphenol; ortho-tertiary butylphenol; 2,6-ditertiary butylphenol; 1,3,5-xylenol, tetramethylphenol; 2-methyl-6-tertiary butylphenol; ortho-phenyl-phenol; ortho-metachlorophenol; ortho-bromophenol; t-chloro-ortho-cresol; 2,6-dichlorophenol. Monohydroxybenzene is obviously the preferred phenolic reactant because of the commercial importance of bisphenol-A.

In addition to acetone, otherwise known as dimethyl ketone, the process of this invention can be carried out by substituting aldehydes or other ketones for acetone. Specific examples include methyl ethyl ketone, methyl propyl ketone, acetophenone, methyl vinyl ketone, cyclopentanone, cyclohexanone, benzophenone, hexalfluoracetone, etc. Again because of the commercial significance of bis-phenol-A, acetone is the preferred reactant.

The drawing is a schematic flow diagram illustrating one example of the process of the present invention. All proportions in the description which follows are on a weight percent basis unless otherwise specified.

Phenol from phenol resevoir 2, a portion of the acetone from resevoir 4, and recycle phenol/p,p-bisphenol-A /o,p-bisphenol-A plus steady state reaction by-products from the ion-exchange isomerizer 28 are charged to ion-exchange BPA reactor RxI heated to a temperature of about 70° C. The effluent from the reactor is passed to a second ion exchange reactor RxII heated to a temperature of about 70° C. Effluent from the first reactor is passed to a second reactor RxII then optionally to subsequent reactors with the addition of the remaining acetone at said reactors. The effluent condensation product stream 8 of bis-phenol-A from the ion exchange reactor RxII containing bisphenol-A, unreacted phenol and acetone, water, color bodies, tars and other reaction by-product impurities is passed to acetone/water/phenol evaporator unit 10. The acetone/phenol/water mixture is stripped of water and the anhydrous acetone stream 12 and phenol stream 14 are recycled to the BPA reactor RxI. Waste water stream 16 is purged. Bottom product stream 18 containing crude bisphenol-A, phenol, color bodies, tars and other by-products is crystallized to yield a 1:1 molar adduct complex of phenol and bis-phenol-A in crystallizer 20. The mother liquid and 1:1 adduct are separated in centrifuge 22. A phenol wash 24 is given to the adduct crystals in the centrifuge 22. The mother/wash liquor stream 26 containing typically 70-85% phenol, 5 to 15% p,p-bis-phenol-A and the balance being color bodies, tars and by-products is passed to an ion-exchange isomerization reactor 28 for isomerization of a portion of the by-products to p,p-bisphenol-A. A portion of stream 26 is passed via stream 30 to the cracking still 32 and cracked to yield phenol, stream 34, and tar-fuel, stream 36, at a temperature from 150°-300° C. in the presence of a suspended aluminum alkoxide cracking catalyst. The overhead phenol stream 34 from the cracking distillation unit is combined with the balance mother/wash liquor stream 38 from the adduct crystallization step. This combined stream is passed through the ion-exchange isomerization reactor 28 for rearrangement of condensation reaction products to p,p-bisphenol-A. The product of the isomerizer RxV is recycled to RxI via stream 40. Residual tars stream 36 is ultimately disposed of. Crude bisphenol-A after separation as a 1:1 molar BPA/phenol crystalline adduct is removed from centrifuge 22 via stream 42. Phenol is removed from the adduct in the stripper 44. The overhead phenol stream 64 is recycled back to the reactor system.

Pure bisphenol-A is crystallized in crystallizer 50 from crude bisphenol-A stream 46 in the presence of water from stream 48. The crystals are separated from the slurry stream 52 in centrifuge 56. An organic solvent wash is given to the crystals to remvoe the surface impurities. High purity bisphenol-A product crystals 58 are dried in drier 60 and packaged 62 for use in the preparation of polycarbonate and/or other polymers. The mother/wash liquors stream 66 from the centrifuge 56 is sent to the organics recovery unit 68 for recovery of the organic solvent 70, bisphenol-A/phenol stream 72 with residual impurities and color bodies and aqueous stream 74, which are recycled to the organic solvent wash 54, adduct crystallizer 20 and the aqueous crystallizer 50, respectively.

The following specific examples illustrate the process of this invention.

EXAMPLES

Two 25 mm diameter tubular glass reactors were connected in series. Isothermal operation was maintained in each reactor by circulating hot oil through the reactor jacket. The catalyst used was microreticular sulfonated polystrene divinyl benzene ion-exchange resin (Amberlite-118 ®) with about 10% of its acid sites neutralized with 2-mercapto-ethylamine. The catalyst loading in each reactor was 40 grams dry weight basis and had a mesh size range from 28-48. All of the phenol required was charged to the first reactor while acetone was injected to both of the reactors. The phenol to acetone ratio was 8.4:1. Flow rate through the reactors was so maintained that fixed acetone conversion/bisphenol-A production per unit time was obtained. Reactor temperature was maintained at 67° C.

High pressure liquid chromotagrophy and ultraviolet spectroscopy was used for reactor effluent component analysis and color analysis, respectively. The color of the reaction mixture was measured by finding the absorbance value of a 10% sample solution in methanol (i.e. 5 gm sample diluted with 50 ml methanol) at 350 nm wavelength and 10 cm pathlength in a Varian Cary 219 spectrophotometer. Table 1 illustrates the effects of varying the percentage of the total acetone injected into the first reactor or the second reactor on the reactor effluent product distribution between p,p-BPA, o,p-BPA and by-products and effluent color. The overall acetone conversion was about 66% in all examples.

TABLE I

| EXAMPLE | ACETONE (wt %) | | EFFLUENT PRODUCT DISTRIBUTION (wt %) | | | ΔCOLOR (ABSORBANCE EFFLUENT-ABSORBANCE FEED) |
|---|---|---|---|---|---|---|
| | 1st $R_x$ | 2nd $R_x$ | p,p-BPA | o,p-BPA | Others* | |
| 1 | 100 | — | 94.6 | 4.1 | 1.3 | 0.0870 |
| 2 | 75 | 25 | 94.9 | 4.2 | 0.9 | 0.0745 |
| 3 | 50 | 50 | 95.1 | 4.3 | 0.6 | 0.0634 |
| 4 | 25 | 75 | 95.3 | 4.3 | 0.4 | 0.0581 |

*The remainder consists of typical condensation by-products, e.g., BPXI, BPXII, spirobiindane, IPP dimers, chromanes, etc.

As illustrated in Table I in Examples 1-4, under steady state reaction conditions, the production of p,p-bisphenol-A is increased with a concurrent decrease in by-products formation by injecting a portion of the acetone reactant into the second reactor. p,p-bisphenol-A is formed in yields of at least about 94 percent p,p-bisphenol-A plus o,p-bisphenol-A are formed in combined yields of at least 98 to 99 percent, while by-products, deleterious to the color, oxidation and thermal stability of the ultimate polycarbonate end product are significantly limited in amounts.

Table II compares the results of the BPA process of Example I using an 8.4 to 1 phenol to acetone molar ratio and no multiple acetone injection with the results of Example 5 using only a 6.3 to 1 phenol to acetone molar ratio with the acetone being distributed 50%—50% between a first and a second reaction vessel. All other reaction conditions were kept constant.

TABLE II

| PRODUCT DISTRI. | EXAMPLE #1 PHENOL/ACETONE 8.4:1 (NO MULTIPLE INJECTION) (100%-0%) | EXAMPLE #5 PHENOL/ACETONE 6.3:1 (MULTIPLE INJECTION) (50%-50%) |
|---|---|---|
| p,p-BPA | 94.60% | 94.70% |
| o,p-BPA | 4.10% | 4.00% |

TABLE II-continued

| PRODUCT DISTRI. | EXAMPLE #1 PHENOL/ACETONE 8.4:1 (NO MULTIPLE INJECTION) (100%-0%) | EXAMPLE #5 PHENOL/ACETONE 6.3:1 (MULTIPLE INJECTION) (50%-50%) |
|---|---|---|
| Others | 1.3% | 1.3% |

Multiple acetone injection in Example 5 also resulted in equivalent color quality of the reactor effluent.

It can be seen from Table II that by using the multiple acetone injection process of the present invention the overall phenol to acetone ratio may be reduced by 25% with no corresponding increase in by-product formation. This means that considerably less phenol has to be recovered and recycled to the reactors which translates to considerable savings in energy and capital. The attendant benefits of reducing by-product formation and color body production are (1) a reduced amount of by-product and color bodies in the system, (2) a reduced amount of by-product is eventually purged as ultimate tar and (3) the amount of product purification necessary for the production of high purity p,p-bisphenol-A, suitable for commercial polycarbonate polymer production, is reduced.

While the invention is described with respect to a particularly preferred embodiment it will be apparent to those of ordinary skill in the art that certain modifications and changes may be made without departing from the spirot instilled in the invention and therefore it is intended that the foregoing disclosure be limited only to the claims appended hereto.

What is claimed is:

1. A process for the preparation of bisphenol-A comprising reacting 5-10 moles of phenol per mole of acetone at a temperature of about 50° C. to about 120° C. in the presence of a cation exchange resin catalyst in a series of reactors wherein all of said phenol and from about 25% to about 75% by weight of said acetone necessary for the reaction is charged to a first reactor and the remainder of said acetone is charged to a subsequent reactor whereby a reduction in color bodies and by-products in the bisphenol-A effluent is achieved and the ratio of phenol to acetone necessary to produce an optimized yield of bisphenol-A is reduced.

2. The process of claim 1 wherein the catalyst is a 2-mercapto-ethyl amine modified microeticular sulfonated polystyrene divinyl benzene ion-exchange resin.

3. The process of claim 1 wherein the catalyst is a sulfonated polystyrene divinyl benzene ion-exchange resin.

4. The process of claim 1 wherein the weight hourly space velocity through the reactor is between about 0.05 to about 15 parts by weight of feed stream per part by weight of catalyst per hour.

5. The process of claim 1 wherein the reaction temperature is between about 60° C. and about 80° C.

6. A process for the production of bis(hydroxyphenyl) alkanes such that a phenolic compound having at least one replaceable hydrogen atom attached directly to a carbon atom in a phenolic ring is reacted at a temperature of about 50° C. to about 120° C. with an aliphatic ketone in the presence of a cation exchange resin catalyst in a reactor or a series of reactors wherein all of said phenolic compound and a portion of said aliphatic ketone necessary for the reaction is charged at the beginning of the reactor and the remainder of said aliphatic ketone is injected along the reactor length or in a subsequent reactor.

7. The process for the preparation of 2,2'-di(hydroxyphenyl)propane comprising reacting phenol and acetone in the presence of a 2-mercapto-ethyl amine modified microreticular sulfonated polystyrene divinyl benzene ion-exchange resin catalyst at the temperature of between about 60° C. and about 80° C. in a reactor or a series of reactors wherein all of said phenol and a portion of said acetone necessary is charged at the beginning of the reactor or the first reactor and the remainder of said acetone is injected along the reactor length or in a subsequent reactor.

* * * * *